(12) United States Patent
Woo

(10) Patent No.: US 9,840,262 B2
(45) Date of Patent: Dec. 12, 2017

(54) ULTRASONIC IMAGING DEVICE

(71) Applicant: SAMSUNG MEDISON CO., LTD., Gangwon-do (KR)

(72) Inventor: Kyeong Gu Woo, Suwon-si (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 0 days.

(21) Appl. No.: 14/793,609

(22) Filed: Jul. 7, 2015

(65) Prior Publication Data
US 2016/0200336 A1 Jul. 14, 2016

(30) Foreign Application Priority Data

Jan. 14, 2015 (KR) .................. 10-2015-0006798

(51) Int. Cl.
*B62B 3/00* (2006.01)
*B62B 5/00* (2006.01)
*A61B 8/00* (2006.01)

(52) U.S. Cl.
CPC ............ *B62B 3/001* (2013.01); *A61B 8/4405* (2013.01); *B62B 5/00* (2013.01)

(58) Field of Classification Search
CPC ........... A61B 8/4405; B62B 3/00; B62B 5/00; B62B 5/0404; B62B 5/0433; B62B 5/0438; B62B 5/0457; B62B 5/061
USPC .......................................................... 701/36
See application file for complete search history.

(56) References Cited

U.S. PATENT DOCUMENTS

| | | | | |
|---|---|---|---|---|
| 5,174,415 A | * | 12/1992 | Neagle | B66F 9/07563 180/209 |
| 6,683,784 B1 | * | 1/2004 | Bidwell | A61B 8/00 248/122.1 |
| 2004/0085715 A1 | | 5/2004 | Bidwell et al. | |
| 2007/0044272 A1 | * | 3/2007 | Misin | B60B 33/0018 16/35 R |
| 2010/0172477 A1 | * | 7/2010 | Kusner | A61B 6/032 378/198 |
| 2013/0194072 A1 | * | 8/2013 | Kim | G08B 5/36 340/6.1 |
| 2015/0257651 A1 | * | 9/2015 | Angott | A61B 5/0091 600/474 |

* cited by examiner

*Primary Examiner* — Redhwan K Mawari
*Assistant Examiner* — Anshul Sood
(74) *Attorney, Agent, or Firm* — McDermott Will & Emery LLP

(57) ABSTRACT

There is provided an ultrasonic imaging device capable of controlling a moving device according to a movement direction of a platform in the front or the rear thereof. An ultrasonic imaging device includes a platform to which an ultrasound probe is connected, a moving device configured to move the platform, and a manipulation unit configured to control the moving device to be in any mode of an aligned movement mode, a free movement mode and a stop mode, wherein the manipulation unit includes a first manipulation unit that is provided in a first direction of the platform and controls operations of the moving device and a second manipulation unit that is provided in a second direction facing the first direction of the platform and controls operations of the moving device.

25 Claims, 8 Drawing Sheets

ULTRASONIC IMAGING DEVICE

CROSS-REFERENCE TO RELATED APPLICATION

This application claims the benefit of Korean Patent Application No. 10-2015-0006798, filed on Jan. 14, 2015 in the Korean Intellectual Property Office, the disclosure of which is incorporated herein by reference.

BACKGROUND

1. Field

Embodiments of the present invention relate to an ultrasonic imaging device.

2. Description of the Related Art

An ultrasonic imaging device is a device that radiates an ultrasound signal to a target area inside a body from a body surface of a subject, uses information on a reflected ultrasound signal (ultrasound echo signal), and obtains a tomogram of soft tissues or an image of blood flow in a non-invasive manner.

The ultrasonic imaging device is advantageous in that it is small and inexpensive, can display in real time, and is highly safe because it involves no exposure to radiation, compared to other image diagnostic devices such as an X-ray diagnostic device, an X-ray computerized tomography scanner (CT scanner), a magnetic resonance imaging (MRI) device, and a nuclear medicine diagnostic device. Due to these advantages, ultrasonic imaging devices are being widely used for cardiac, abdominal, urogenital, and obstetric diagnoses.

SUMMARY

According to an embodiment of the present invention, there is provided an ultrasonic imaging device capable of controlling a moving device according to a movement direction of a platform in the front or the rear.

According to an aspect of the present invention, there is provided an ultrasonic imaging device, including a platform to which an ultrasound probe is connected, a moving device configured to move the platform, and a manipulation unit configured to control the moving device to be in any mode of an aligned movement mode, a free movement mode and a stop mode, wherein the manipulation unit includes a first manipulation unit that is provided in a first direction of the platform and controls operations of the moving device and a second manipulation unit that is provided in a second direction facing the first direction of the platform and controls operations of the moving device.

By manipulating any of the first manipulation unit and the second manipulation unit, the caster may be controlled to be in any mode of an aligned movement mode, a free movement mode and a stop mode.

The moving device may be a caster that is rotatable in all directions.

The manipulation unit may include an aligned movement button, a free movement button and a stop button.

By manipulating the aligned movement button provided in the first manipulation unit, a moving device provided in a second direction of the platform may be aligned to move the platform in the second direction.

By manipulating the aligned movement button provided in the second manipulation unit, a moving device provided in a first direction of the platform may be aligned to move the platform in the first direction.

By manipulating at least one of a free movement button provided in the first manipulation unit and a free movement button provided in the second manipulation unit, the moving device may be rotatable in all directions.

By manipulating at least one of the stop button provided in the first manipulation unit and the stop button provided in the second manipulation unit, the moving device may be locked by a locking unit not to rotate.

The platform may include a handle unit.

The handle unit may be provided in the first direction and in the second direction of the platform.

At least one of the first manipulation unit and the second manipulation unit may be provided in the handle unit.

At least one of the first manipulation unit and the second manipulation unit may include a foot pedal.

The moving device may include a sensor configured to detect operations of the moving device.

According to the result detected by the sensor, the moving device may be provided to be in any mode of the aligned movement mode, the free movement mode and the stop mode.

When the sensor detects that the moving device rotates to move in the first direction, the moving device positioned in the first direction of the platform may be aligned, and when the sensor detects that the moving device rotates to move in the second direction, the moving device positioned in the second direction of the platform may be aligned.

According to another aspect of the present invention, there is provided an ultrasonic imaging device including a platform to which an ultrasound probe is connected to obtain an ultrasound image. The platform includes a plurality of casters that are rotatable in all directions and a manipulation unit configured to control the plurality of casters to rotate in a specific direction. The manipulation unit includes a first manipulation unit positioned in a first direction of the platform and a second manipulation unit positioned in a second direction of the platform.

By manipulating the first manipulation unit, the caster positioned in the second direction of the platform may be aligned to move the platform in the second direction.

By manipulating the second manipulation unit, the caster positioned in the first direction of the platform may be aligned to move the platform in the first direction.

The first manipulation unit and the second manipulation unit may include a stop button enabling the caster to be locked.

The first manipulation unit and the second manipulation unit may include a free movement button enabling an aligned state or a locking state of the caster to be released.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Hereinafter, an ultrasonic imaging device according to an embodiment of the present invention will be described in detail with reference to the drawings.

Figure 1:
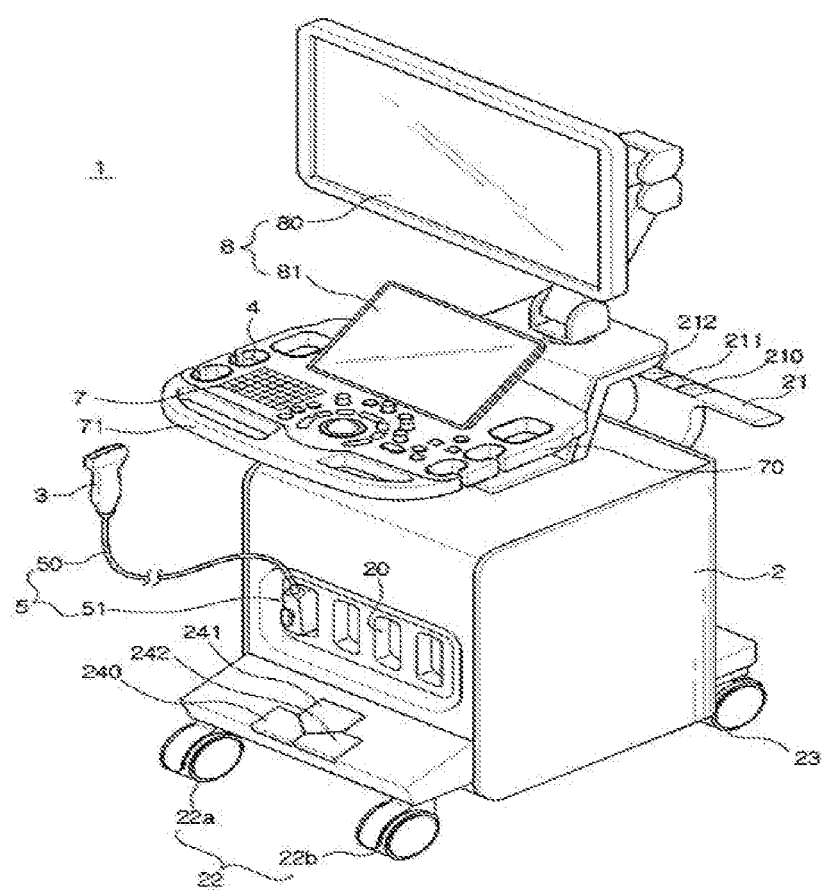
FIG. 1 is a diagram illustrating an ultrasonic imaging device according to an embodiment of the present invention.

FIG. 1 is a diagram illustrating an ultrasonic imaging device according to an embodiment of the present invention.

As illustrated in FIG. 1, an ultrasonic imaging device 1 according to the embodiment of the present invention may include a platform 2, an ultrasound probe 3, an input unit 7 and a display 8. The display 8 may include a main display 80 and a sub display 81.

The display 8 may display an ultrasound image obtained in an ultrasound diagnostic process. Also, the display 8 may display an application related to operations of the ultrasonic imaging device 1. As an example, the main display 80 may display the ultrasound image obtained in the ultrasound diagnostic process. The sub display 81 may display content related to operations of the ultrasonic imaging device 1.

The main display 80 or the sub display 81 may be implemented by a cathode ray tube (CRT), a liquid crystal display (LCD) or the like. The main display 80 or the sub display 81 may be provided in combination with the platform 2, or provided separately from the platform 2.

The platform 2 may include the input unit 7. The input unit 7 may be provided in the form of a keyboard, a button, a dial, a foot switch or a foot pedal. When the input unit 7 is the keyboard, it may be provided above the platform 2. When the input unit 7 is the foot switch or the foot pedal, it may be provided below the platform 2. An operator may control operations of the ultrasonic imaging device 1 through the input unit 7.

In the input unit 7, a keyboard, a button, a dial and the like may be provided in an input panel 70. The input panel 70 may be mounted on the platform 2. A handle unit 71 may be provided at one end of the input panel 70. A user grasps the handle unit 71 and applies a force to move the ultrasonic imaging device 1.

The ultrasound probe 3 may be connected to the platform 2 by a connecting member 5. The connecting member 5 includes a cable 50 and a connector 51. The ultrasound probe 3 may be provided at one end of the cable 50. The connector 51 may be provided at the other end of the cable 50. The connector 51 may be detachably mounted on a connecting unit 20 provided in the platform 2. Therefore, the ultrasound probe 3 and the platform 2 may be connected.

A placing unit 4 enabling the ultrasound probe 3 to be placed on the platform 2 may be provided at one end of the ultrasonic imaging device 1. When the ultrasonic imaging device 1 is not used, the operator may place and keep the ultrasound probe 3 on the placing unit 4. As an example, the placing unit 4 may be provided in the form of a hole through which a handgrip part of the ultrasound probe 3 can pass in the input panel 70. The ultrasound probe 3 may be inserted into the hole formed in the input panel 70 and placed therein. As another example, the placing unit 4 may be provided in the form of a holder mounted on the platform 2. The ultrasound probe 3 may be inserted into the holder and placed therein.

A moving device capable of moving the ultrasonic imaging device 1 may be provided in the platform 2. The moving device may include a plurality of casters 22 and 23. The casters 22 and 23 may be aligned (aligned movement mode) in order to advance the platform 2 in a specific direction, be provided to be freely movable (free movement mode), or be locked (stop mode) in order to stop the platform 2 at a specific position. Details thereof will be described below.

The casters 22 and 23 may include the first caster 22 and the second caster 23. A direction in which the input unit 7 and the display 8 are positioned is defined as a first direction. When a direction facing the first direction is set as a second direction, the first caster 22 may be positioned in the first direction of the platform 2, and the second caster 23 may be positioned in the second direction of the platform 2. First casters 22a and 22b may be provided on the left and right in the first direction of the platform 2. Second casters 23a and 23b (refer to FIGS. 2A to 2C) may be provided on the left and right in the second direction of the platform 2 to correspond to the first casters 22a and 22b.

In the platform 2, handle units 21 and 71 that the user grasps to move the ultrasonic imaging device 1 may be provided in the first direction and the second direction, respectively. The handle units 21 and 71 may include the first handle unit 71 provided in the first direction of the platform 2 and the second handle unit 21 provided in the second direction of the platform 2. The first handle unit 71 may be provided at one end of the input panel 70. The second handle unit 21 may be provided to protrude in the second direction of the platform 2.

Manipulation units capable of controlling the casters 22 and 23 may be provided in the platform 2. The manipulation units may be provided in each of the first direction and the second direction of the platform 2. First manipulation units 240, 241, and 242 may be provided in the first direction of the platform 2. Second manipulation units 210, 211, and 212 may be provided in the second direction of the platform 2.

Each of the manipulation units may be provided in the form of a foot pedal, a button, a dial and the like. As an example, the first manipulation units 240, 241, and 242 may be provided in the form of foot pedals, and the second manipulation units 210, 211, and 212 may be provided in the form of buttons. The first manipulation units 240, 241, and 242 may be provided in a lower part of the platform 2 in the first direction.

The user stands in the first direction of the platform 2, steps on and manipulates the foot pedal with his or her foot, and then grasps the first handle unit 71 to move or stop the ultrasonic imaging device 1. The second manipulation units 210, 211, and 212 may be provided in the second handle unit 21. The user may manipulate the button provided in the second handle unit 21 and then grasp the second handle unit 21 to move or stop the ultrasonic imaging device 1.

In this manner, the handle units that the user can manipulate and the manipulation units with which the user can change an operation mode of the caster are provided in the first direction and the second direction, respectively. Therefore, the ultrasonic imaging device 1 can be easily moved.

In the related art, handle units are provided in the first direction and the second direction, but a manipulation unit capable of changing an operation mode of the caster is provided in only one direction of the first direction and the second direction. In this case, even when the user grasps the handle unit positioned in the second direction to move the ultrasonic imaging device, the manipulation unit positioned in the first direction is manipulated, an operation mode of the caster is changed, and the user moves in the second direction and grasps the handgrip provided in the second direction to move the ultrasonic imaging device, which causes inconvenience in moving the ultrasonic imaging device.

However, when the ultrasonic imaging device 1 according to the embodiment of the present invention is used, the handle units and the manipulation units are provided in the first direction and the second direction of the platform 2, respectively. Therefore, controlling and operating the moving device of the ultrasonic imaging device may be performed in one direction. As an example, the first direction of the platform 2 may be defined as forward, and the second direction may be defined as backward.

Hereinafter, a structure of the manipulation unit and operations of the manipulation unit when the ultrasonic imaging device 1 is in an aligned movement mode, a free movement mode, or a stop mode will be described.

Figure 2A:
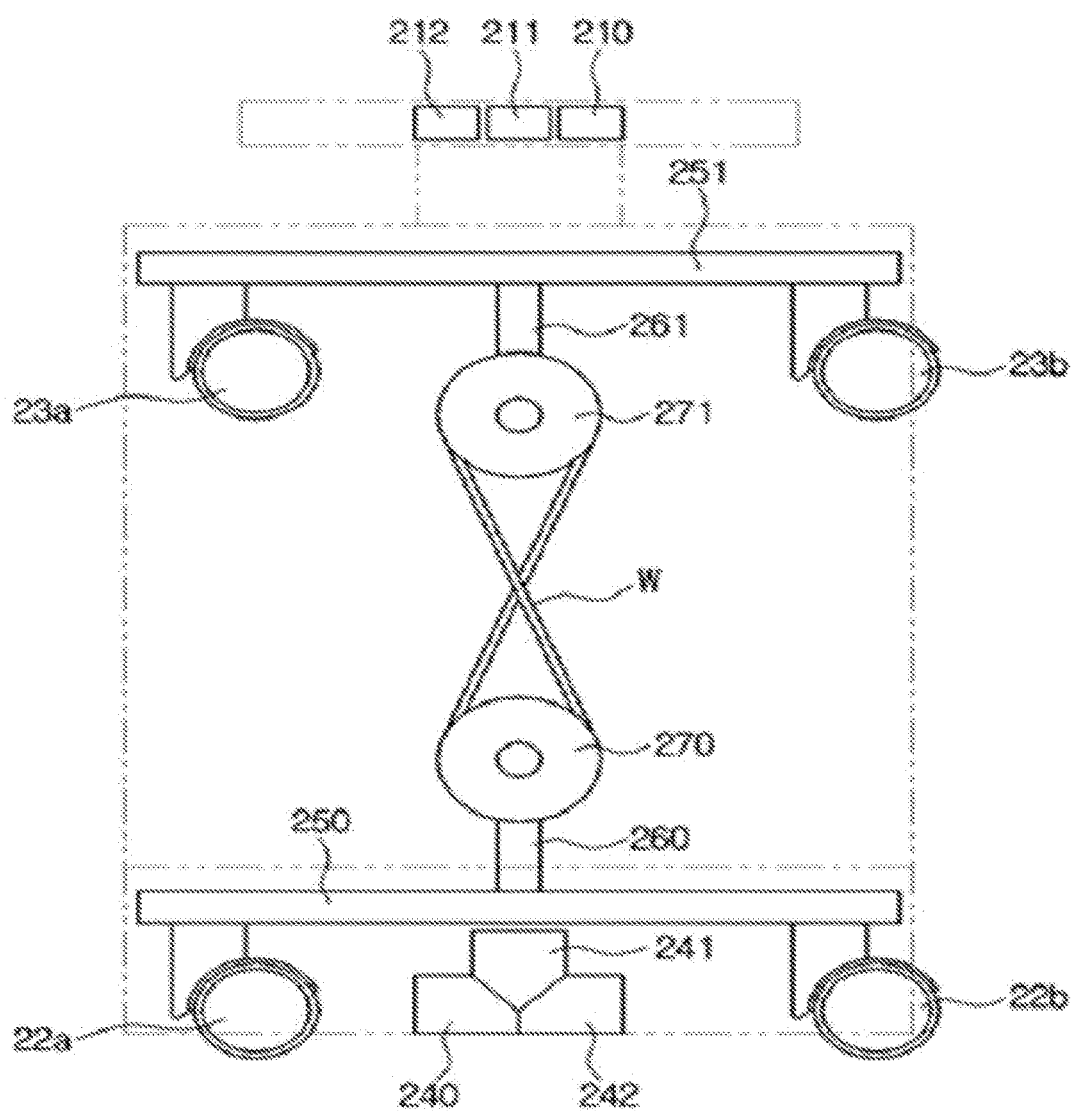
FIGS. 2A to 2C are diagrams schematically illustrating a moving device of an ultrasonic imaging device according to an embodiment of the present invention.
Figure 2B:
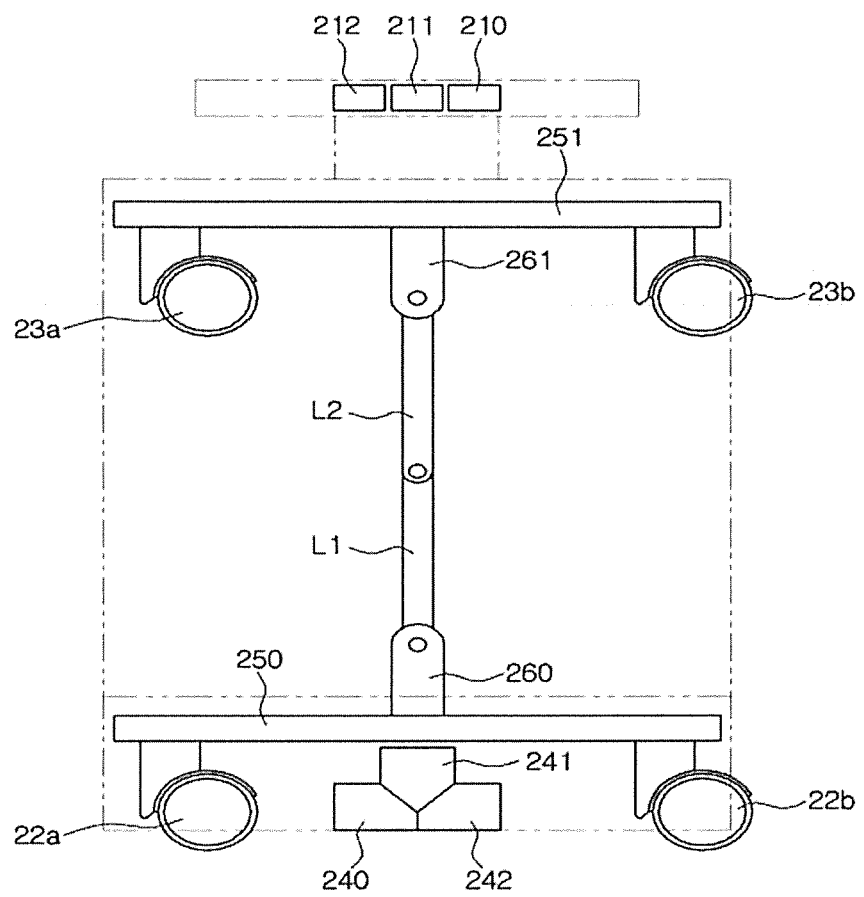
Figure 2C:
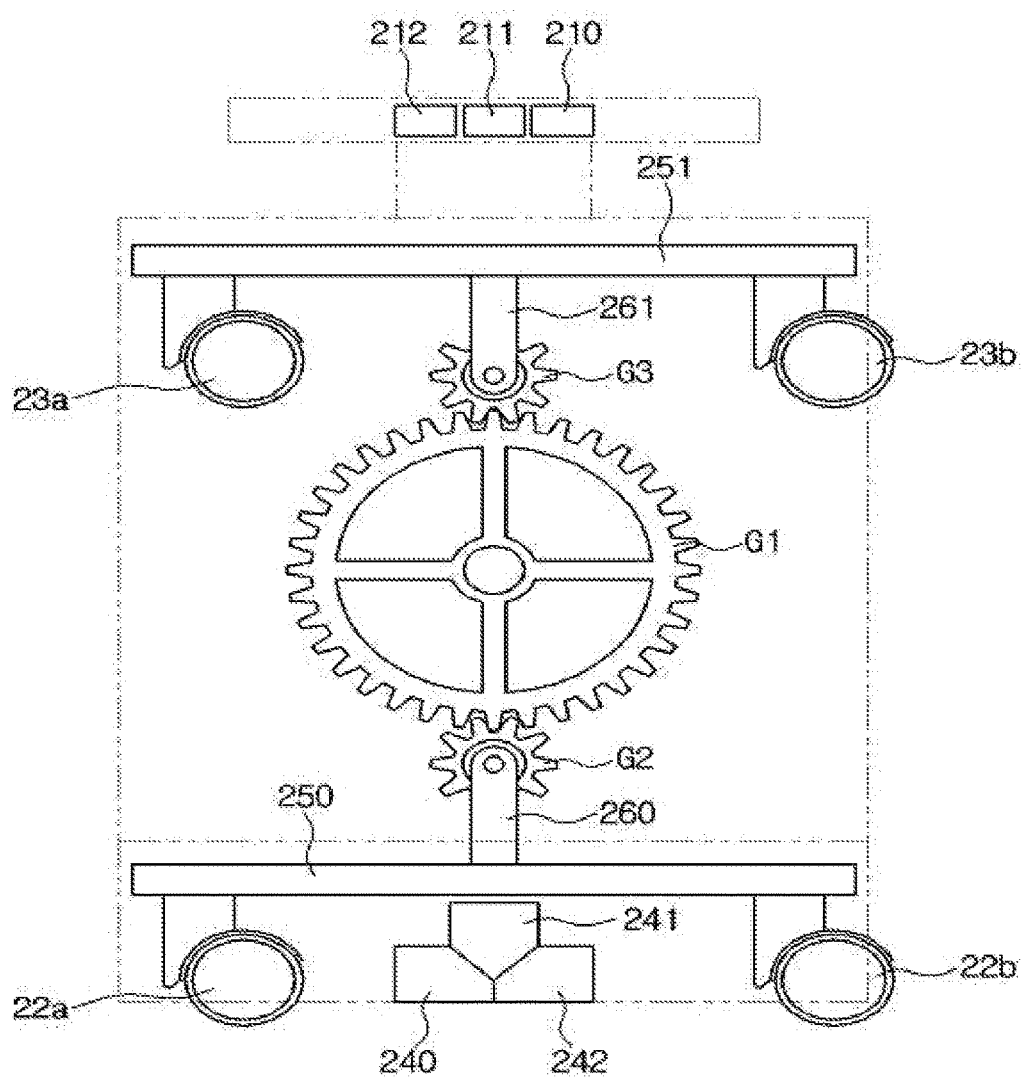

FIGS. 2A to 2C are diagrams schematically illustrating a moving device of an ultrasonic imaging device according to an embodiment of the present invention.

As illustrated in FIGS. 2A to 2C, the moving device of the ultrasonic imaging device 1 according to the embodiment of the present invention includes the first casters 22a and 22b positioned in a first direction F and the second casters 23a and 23b positioned in a second direction R. The two first casters 22a and 22b positioned on the left and right are connected by a first link 250, and may be operated in the same mode according to manipulation of the handle units 21 and 71. Similarly, the two second casters 23a and 23b positioned on the left and right are connected by a second link 251, and may be operated in the same mode according to manipulation of the handle units 21 and 71.

Clutches 260 and 261 may be connected to the first link 250 and the second link 251, respectively. The clutches 260 and 261 may include the first clutch 260 connected to the first link 250 and the second clutch 261 connected to the second link 251.

A control operation according to manipulation of the first manipulation units 240, 241, and 242 may be selectively delivered to the first link 250 by the first clutch 260. An operation mode of the first caster 22 may be switched only when a control operation by the first manipulation units 240, 241, and 242 is delivered to the first link 250. That is, the first caster 22 may be switched from any operation mode between stop and free movement modes to the aligned movement mode only when the control operation by the first manipulation units 240, 241, and 242 is delivered to the first link 250.

Similarly, a control operation according to manipulation of the second manipulation units 210, 211, and 212 may be selectively delivered to the second link 251 by the second clutch 261. An operation mode of the second caster 23 may be switched only when a control operation by the second manipulation units 210, 211, and 212 is delivered to the second link 251. That is, the second caster 23 may be switched from any operation mode between stop and free movement modes to the aligned movement mode only when the control operation by the second manipulation units 210, 211, and 212 is delivered to the second link 251.

As illustrated in FIG. 2A, a first pulley 270 may be provided in the first direction of the platform 2, and a second pulley 271 may be provided in the second direction. The first pulley 270 and the second pulley 271 may be connected through a cable W. The control operation according to manipulation of the first manipulation units 240, 241, and 242 may be delivered to the second link 251 through the first pulley 270 and the cable W. The control operation by the second manipulation units 210, 211, and 212 may be delivered to the first link 250 through the second pulley 271 and the cable W.

As illustrated in FIG. 2B, the first link 250 and the second link 251 may be connected by link members L1 and L2. As illustrated in FIG. 2C, the first link 250 and the second link 251 may be connected by gears G1, G2, and G3.

The structure connecting the first link 250 and the second link 251, which enables the control operation according to manipulation of the manipulation units to be delivered, is not limited to the above structure. A structure in which the first link 250 and the second link 251 are connected through the cable W will be described below with reference to FIG. 2A.

Controlling and operating the moving device when the ultrasonic imaging device 1 according to the embodiment of the present invention is moved in a specific direction will be described below.

Figure 3:
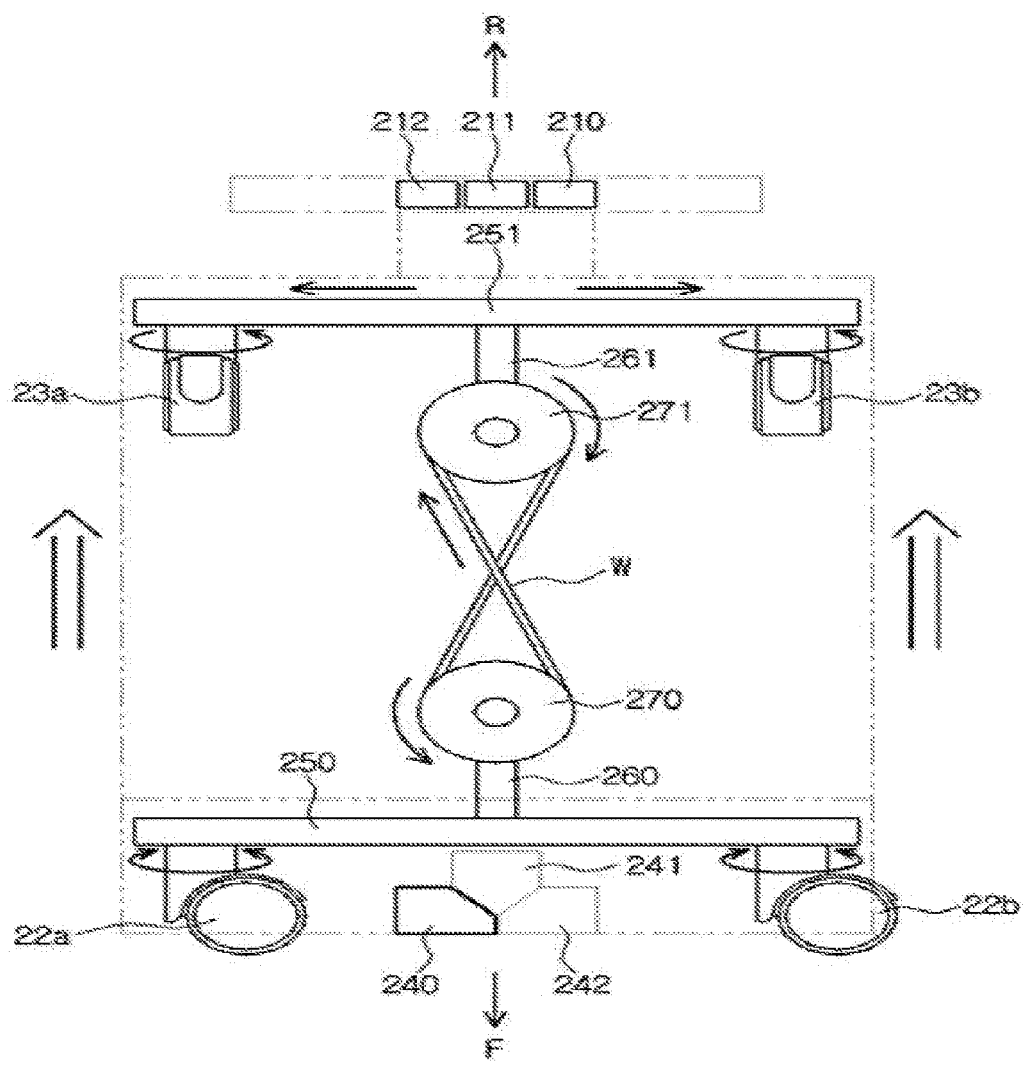
FIG. 3 is a diagram schematically illustrating a state of a moving device when an ultrasonic imaging device according to an embodiment of the present invention is in an aligned movement mode.

FIG. 3 is a diagram schematically illustrating a state of a moving device when an ultrasonic imaging device according to an embodiment of the present invention is in an aligned movement mode.

As illustrated in FIG. 3, in order to move the ultrasonic imaging device 1 according to the embodiment of the present invention in the second direction R, the user may grasp the first handle unit 71 in the first direction F and push and move the platform 2 in the second direction R.

Before the platform 2 is moved, the casters 22 and 23 may be in the stop mode or the free movement mode. The user may manipulate the first manipulation units 240, 241, and 242 and switch the second casters 23a and 23b to the aligned movement mode. As an example, the user may press the aligned movement button 240 of the first manipulation units 240, 241, and 242 and align the second casters 23a and 23b to move the platform 2 in the second direction R. When the second casters 23a and 23b are aligned, the second casters 23a and 23b may rotate and move only in the second direction R. In this case, the first casters 22a and 22b may be rotatable in all directions.

When the user presses the aligned movement button 240 while the casters 22 and 23 are in the stop mode, the first casters 22a and 22b may release a locking state of a first locking unit 220 (refer to FIG. 5), and the second casters 23a and 23b may be aligned to rotate and be moved in the second direction R.

In this case, the first clutch 260 may be turned off, and the second clutch 261 may be turned on. When the aligned movement button 240 is pressed, the first pulley 270 may rotate according to an internal configuration in which the aligned movement button 240 and the first pulley 270 are connected. A rotational force of the first pulley 270 may be delivered to the second pulley 271 through the cable W. Since the second clutch 261 is turned on, the rotational force applied to the second pulley 271 may be delivered to the second link 251. By the rotational force delivered to the second link 251, the second casters 23a and 23b may be aligned to move in the second direction R. As long as neither the stop button nor the free movement button of the manipulation unit is pressed, the second casters 23a and 23b may remain aligned to move in the second direction R.

Since the first clutch 260 is turned off, the rotational force of the first pulley 270 is not delivered to the first link 250. The first casters 22a and 22b are not aligned to rotate in only a specific direction but are freely rotatable in all directions.

The operation in which the user stands in the first direction F and manipulates the first manipulation unit in order to move the ultrasonic imaging device 1 in the second direction R, and grasps the first handle unit 71 and moves the platform 2 in the second direction R has been described above.

Similarly, in order to move the ultrasonic imaging device 1 in the first direction F, the user may stand in the second direction R, press the aligned movement button 210 of the second manipulation unit, grasp the second handle unit 21, and move the platform 2 in the first direction F. In this case, the first clutch 260 may be turned on and the second clutch 261 may be turned off. The first casters 22a and 22b may rotate and remain aligned to move in the first direction F, and the second casters 23a and 23b may rotate in all directions.

An internal configuration in which a driving force is delivered to the first pulley 270 by manipulation of the aligned movement button 240 of the related art may be used. Therefore, details thereof will not be described.

Figure 4:
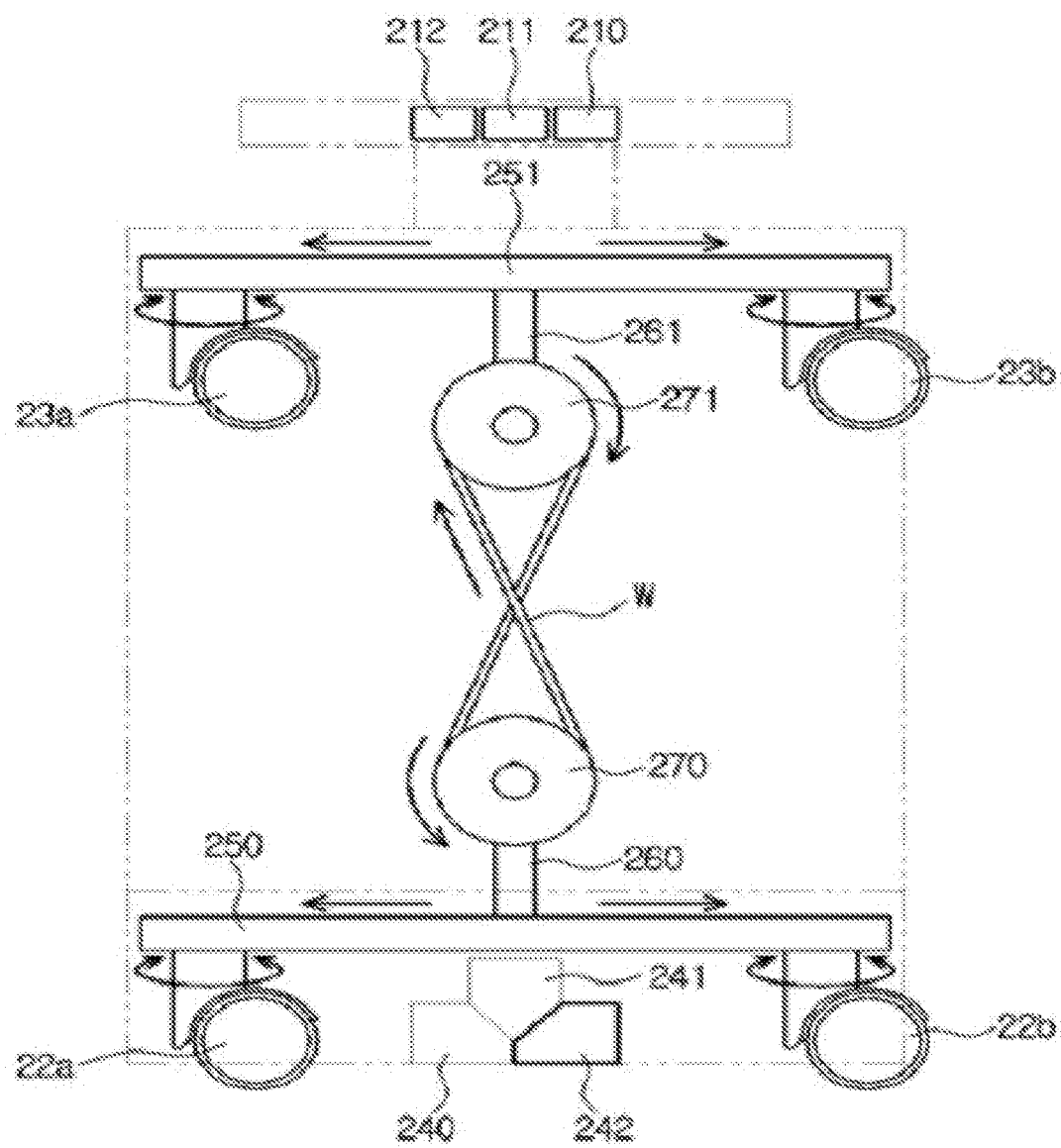
FIG. 4 is a diagram schematically illustrating a state of a moving device when an ultrasonic imaging device according to an embodiment of the present invention is in a free movement mode.

FIG. 4 is a diagram schematically illustrating a state of a moving device when an ultrasonic imaging device according to an embodiment of the present invention is in a free movement mode.

As illustrated in FIG. 4, the ultrasonic imaging device 1 according to the embodiment of the present invention may be freely movable in all directions without constraints on an advancing direction. The user may stand in the first direction F with respect to the platform 2 and grasp the first handle unit 71 to move the ultrasonic imaging device 1, or stand in the second direction R and grasp the second handle unit 21 to move the ultrasonic imaging device 1.

As an example, when the user stands in the first direction F of the platform 2 to move the ultrasonic imaging device 1, the user may press a free movement button 242 provided in the first manipulation unit. When the free movement button 242 is pressed, a locking state and an aligned state of the casters 22 and 23 may be released, and the first casters 22a and 22b and the second casters 23a and 23b may be freely rotatable in all directions.

Similarly, when the user stands in the second direction R of the platform 2 to move the ultrasonic imaging device 1, the user may press a free movement button 212 provided in the second manipulation unit. When the free movement button 212 is pressed, a locking state and an aligned state of the casters 22 and 23 may be released, and the first casters 22a and 22b and the second casters 23a and 23b may be freely rotatable in all directions.

In this manner, the user may manipulate the manipulation unit in any direction of the first direction and the second direction, enable the casters 22 and 23 to be freely movable in all directions, and then move the ultrasonic imaging device 1.

Figure 5:
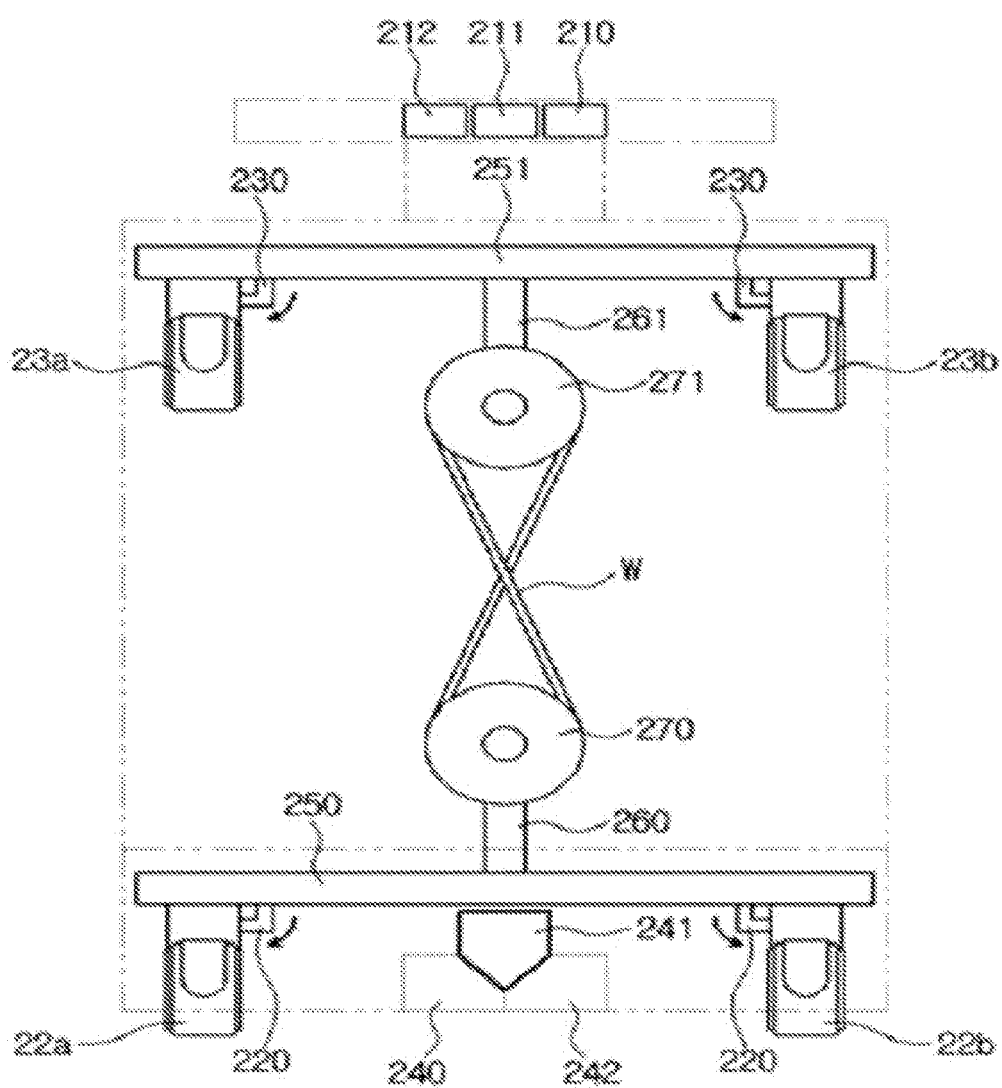
FIG. 5 is a diagram schematically illustrating a state of a moving device when an ultrasonic imaging device according to an embodiment of the present invention is in a stop mode.

FIG. 5 is a diagram schematically illustrating a state of a moving device when an ultrasonic imaging device according to an embodiment of the present invention is in a stop mode.

As illustrated in FIG. 5, in order to fix the ultrasonic imaging device 1 according to the embodiment of the present invention at a specific position, the user may manipulate a stop button 241 provided in the first manipulation unit or a stop button 211 provided in the second manipulation unit.

As an example, the user may move the platform 2 to a desired position in the first direction F of the platform 2 and then press the stop button 241 provided in the first manipulation unit. When the stop button 241 is pressed, the first casters 22a and 22b or the second casters 23a and 23b may be locked by the locking units 220 and 230. When the first casters 22a and 22b or the second casters 23a and 23b are locked by the locking units 220 and 230, the first casters 22a and 22b or the second casters 23a and 23b may be fixed not to rotate.

The locking units 220 and 230 may include the first locking unit 220 configured to lock the first casters 22a and 22b and the second locking unit 230 configured to lock the second casters 23a and 23b. When the stop button 241 is pressed, the first locking unit 220 may lock the first casters 22a and 22b not to rotate, or the second locking unit 230 may lock the second casters 23a and 23b not to rotate. Only one of the first casters 22a and 22b and the second casters 23a and 23b may be locked, or all of the first casters 22a and 22b and the second casters 23a and 23b may be locked.

When the user is positioned in the second direction R of the platform 2, the user may press the stop button 211 provided in the second manipulation unit. Similar to when the stop button 241 provided in the first manipulation unit is pressed, when the stop button 211 provided in the second manipulation unit is pressed, the first locking unit 220 may lock the first casters 22a and 22b not to rotate, or the second locking unit 230 may lock the second casters 23a and 23b not to rotate. In this case, any one of the first casters 22a and 22b and the second casters 23a and 23b may be locked and all of the first casters 22a and 22b and the second casters 23a and 23b may be locked.

The embodiment in which the manipulation units are provided in the first direction and the second direction of the platform 2 has been described above, but the position of the manipulation unit is not limited thereto. The manipulation units may be provided on the left and right of the platform 2.

Figure 6:
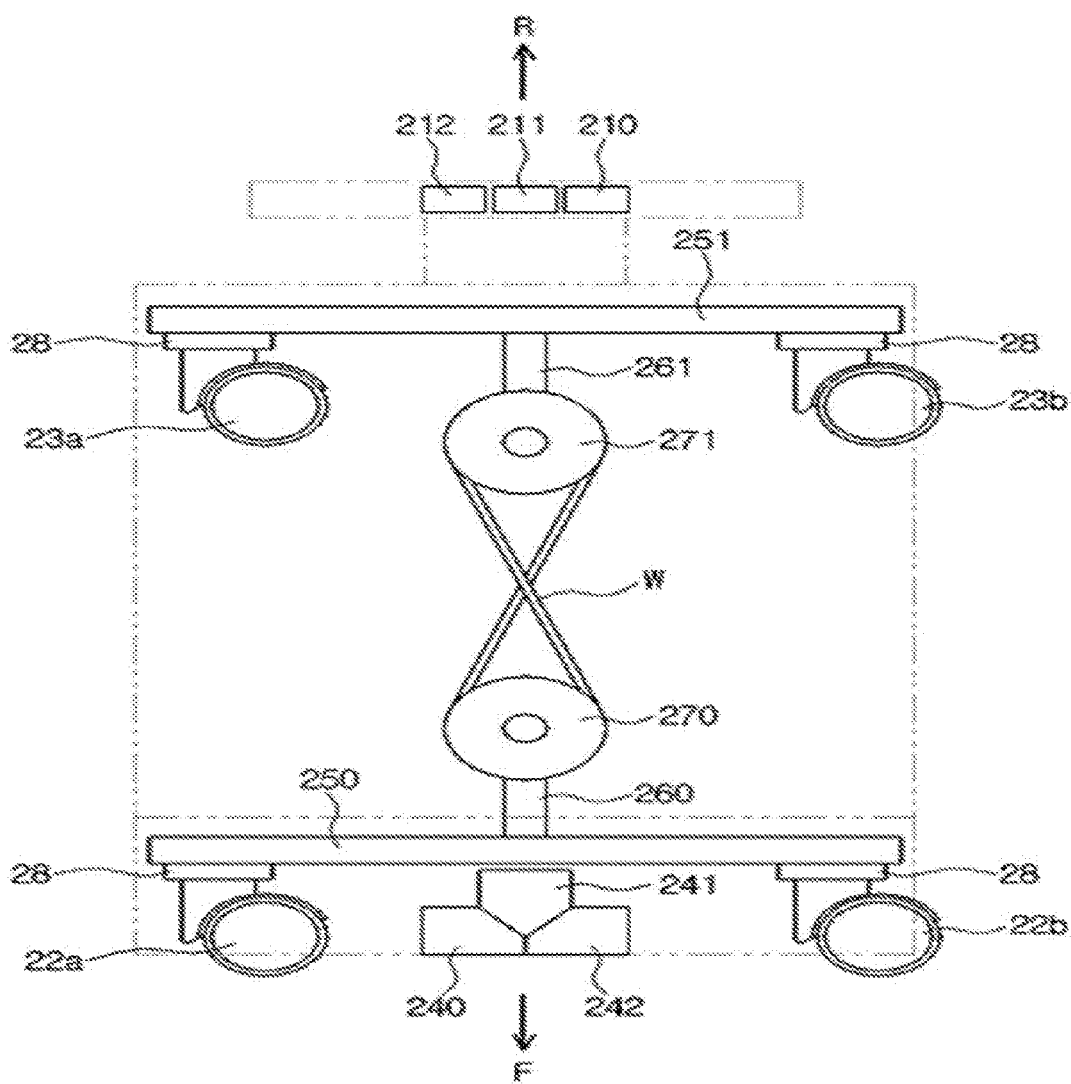
FIG. 6 is a diagram schematically illustrating a state in which a sensor is included in a moving device of an ultrasonic imaging device according to an embodiment of the present invention.

FIG. 6 is a diagram schematically illustrating a state in which a sensor is included in a moving device of an ultrasonic imaging device according to an embodiment of the present invention.

As illustrated in FIG. 6, the ultrasonic imaging device 1 according to the embodiment of the present invention may include a sensor 28 configured to detect rotation of the casters 22 and 23. The sensor 28 may be included in at least one of the first casters 22a and 22b or the second casters 23a and 23b.

When the user grasps the first handle unit 71 or the second handle unit 21 and applies a force to move the ultrasonic imaging device 1, the casters 22 and 23 may be driven to rotate in a specific direction. In this case, the sensor 28 detects a direction in which the casters 22 and 23 rotate due to the applied force, and a control unit (not illustrated) may align the casters 22 and 23 to be rotatable in a specific direction according to the detected result. When the direction in which the casters 22 and 23 rotate due to the applied force is continuously changed, the control unit may perform control such that the casters 22 and 23 rotate in response thereto. Therefore, the casters 22 and 23 may be in the free movement mode. When it is detected that the force applied to the casters 22 and 23 is removed, the control unit may perform control such that the locking units 220 and 230 lock the casters 22 and 23.

In this manner, the sensor 28 is provided to detect operations of the casters 22 and 23 and the casters 22 and 23 are aligned in a specific direction or locked so that the user may easily move the ultrasonic imaging device 1 or enable the ultrasonic imaging device 1 to be stopped at a specific position when the user is positioned in the first direction or the second direction with respect to the platform 2 or regardless of his or her position.

The user manipulates the first manipulation unit or the second manipulation unit of the ultrasonic imaging device 1 according to the embodiment of the present invention at a position in which the user stands, and enables the ultrasonic imaging device 1 to be aligned and move, freely moved or stopped. The manipulation units are provided in the first direction and the second direction to correspond to the first handle unit 71 and the second handle unit 21. Therefore, the user may move or stop the ultrasonic imaging device 1 after manipulating the manipulation unit without the user's movement.

According to an embodiment of the present invention, a function of aligning the caster may be performed in both the front and the rear of the ultrasonic imaging device. Therefore, it is possible to easily control the caster according to a movement direction of the ultrasonic imaging device.

| Reference Numerals | |
|---|---|
| 1: ultrasonic imaging device | 2: platform |
| 3: ultrasound probe | 4: placing unit |
| 5: connecting member | 7: input unit |
| 8: display | 21: second handle unit |
| 22: first caster | 23: second caster |
| 28: sensor | 210: aligned movement button |
| 211: free movement button | 212: stop button |
| 220: first locking unit | 230: second locking unit |
| 240: aligned movement button | 241: free movement button |
| 242: stop button | 260: first clutch |
| 261: second clutch | |
| F: first direction | R: second direction |

What is claimed is:

1. An ultrasonic imaging device comprising:
   a platform;
   a moving device configured to move the platform; and
   a manipulation unit configured to control operations of the moving device,
   wherein the moving device includes a first moving device positioned in the front of the platform in a first direction and a second moving device positioned in the rear of the platform in the first direction,
   wherein the manipulation unit is controlled based on input information received by the manipulation unit, and
   wherein the first moving device is moved to be aligned in the first direction by the manipulation unit and the second moving device is moved to be aligned in a second direction by the manipulation unit in response to the input information.

2. The ultrasonic imaging device according to claim 1, wherein forward in the first direction refers to forward in an advancing direction based on a center of the platform, and backward in the first direction refers to backward in the advancing direction based on the center of the platform.

3. The ultrasonic imaging device according to claim 1, wherein movement in the front or the rear of the platform is detected by a sensor provided in the first moving device or the second moving device.

4. The ultrasonic imaging device according to claim 1, wherein the first moving device or the second moving device is aligned by the manipulation unit.

5. The ultrasonic imaging device according to claim 1, wherein, when the manipulation unit is pressed, a force applied to the manipulation unit is delivered by a transmission member and the moving device is aligned.

6. The ultrasonic imaging device according to claim 1, wherein the moving device is electrically controlled and aligned by an input signal of the manipulation unit.

7. The ultrasonic imaging device according to claim 1, wherein the manipulation unit includes a first manipulation unit positioned in the front of the platform and a second manipulation unit positioned in the rear of the platform.

8. The ultrasonic imaging device according to claim 7, wherein the moving device is rotatable in any direction by manipulating at least one of a free movement input unit provided in the first manipulation unit or a free movement input unit provided in the second manipulation unit.

9. The ultrasonic imaging device according to claim 7, wherein the moving device is locked by a locking unit not to rotate by manipulating at least one of a stop input unit provided in the first manipulation unit or a stop input unit provided in the second manipulation unit.

10. The ultrasonic imaging device according to claim 7, wherein at least one of the first manipulation unit or the second manipulation unit includes a foot pedal.

11. The ultrasonic imaging device according to claim 1, wherein the moving device is a caster that is rotatable in any direction.

12. The ultrasonic imaging device according to claim 1, wherein the manipulation unit includes an aligned movement input unit configured to align the first moving device or the second moving device, a free movement input unit configured to move the first moving device and the second moving device in any direction, and a stop input unit configured to lock at least one of the first moving device and the second moving device.

13. The ultrasonic imaging device according to claim 12, wherein the second moving device provided in the rear of the platform is aligned by manipulating the aligned movement input unit.

14. The ultrasonic imaging device according to claim 12, wherein the first moving device provided in the front of the platform is aligned by manipulating the aligned movement input unit.

15. The ultrasonic imaging device according to claim 1, wherein the platform includes a handle unit.

16. The ultrasonic imaging device according to claim 15, wherein the handle unit is provided in the front and the rear with respect to a direction in which the platform moves.

17. The ultrasonic imaging device according to claim 15, wherein the manipulation unit includes at least one of a first manipulation unit or a second manipulation unit provided in the handle unit.

18. The ultrasonic imaging device according to claim 1, wherein the moving device includes a sensor configured to detect operations of the moving device.

19. The ultrasonic imaging device according to claim 18, wherein the moving device is provided to be in any mode of an aligned movement mode, a free movement mode and a stop mode according to the result detected by the sensor.

20. The ultrasonic imaging device according to claim 19, wherein, when the sensor detects that the moving device rotates to move in the first direction, the first moving device is aligned, and when the sensor detects that the moving device rotates to move in the second direction, the second moving device is aligned.

21. An ultrasonic imaging device comprising:
    a platform;
    a moving device configured to move the platform;
    a sensor configured to detect operations of the moving device; and
    a control unit configured to perform control such that the moving device is aligned in response to detected information received from the sensor,
    wherein the moving device includes a first moving device positioned in the front and a second moving device positioned in the rear with respect to a direction in which the platform moves, and wherein, when the platform moves forward, the first moving device is aligned, and when the platform moves backward, the second moving device is aligned.

22. The ultrasonic imaging device according to claim 21, wherein the control unit performs control such that information detected by the sensor is received to align the moving device, the moving device is movable in any direction, or at least one of the first moving device and the second moving device is locked to stop the platform.

23. The ultrasonic imaging device according to claim 22, wherein an aligned movement input unit that is manipulated to align the moving device, a free movement input unit that is manipulated to move the moving device in any direction, and a stop input unit that is manipulated to stop the moving device are included in the front or the rear of the platform.

24. The ultrasonic imaging device according to claim 21, wherein, when the sensor detects that the moving device is stopped, the moving device is controlled to be in a locking mode.

25. The ultrasonic imaging device according to claim 21, wherein, when the sensor detects that the moving device moves in a plurality of directions, the moving device is controlled to be in a free movement mode.

\* \* \* \* \*